(12) United States Patent
Erkens et al.

(10) Patent No.: US 10,179,093 B2
(45) Date of Patent: Jan. 15, 2019

(54) COMPOSITIONS AND METHODS FOR COLORING KERATINIC FIBERS

(71) Applicant: Henkel AG & Co. KGaA, Duesseldorf (DE)

(72) Inventors: Udo Erkens, Willich (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 4 days.

(21) Appl. No.: 15/526,594

(22) PCT Filed: Oct. 2, 2015

(86) PCT No.: PCT/EP2015/072830
§ 371 (c)(1),
(2) Date: May 12, 2017

(87) PCT Pub. No.: WO2016/074853
PCT Pub. Date: May 19, 2016

(65) Prior Publication Data
US 2017/0312188 A1 Nov. 2, 2017

(30) Foreign Application Priority Data
Nov. 12, 2014 (DE) .................. 10 2014 223 093

(51) Int. Cl.
*A61Q 5/10* (2006.01)
*A61K 8/02* (2006.01)
*A61Q 5/08* (2006.01)
*B65D 65/46* (2006.01)

(52) U.S. Cl.
CPC .............. *A61K 8/0204* (2013.01); *A61Q 5/08* (2013.01); *A61Q 5/10* (2013.01); *B65D 65/46* (2013.01); *A61K 2800/432* (2013.01); *A61K 2800/4322* (2013.01); *A61K 2800/4324* (2013.01); *A61K 2800/56* (2013.01); *A61K 2800/882* (2013.01)

(58) Field of Classification Search
CPC . A61Q 5/08; A61Q 5/10; B65D 65/46; A61K 8/0204; A61K 2800/4322; A61K 2800/4324; A61K 2800/882; A61K 2800/432; A61K 2800/56

See application file for complete search history.

(56) References Cited

U.S. PATENT DOCUMENTS

| | | |
|---|---|---|
| 3,892,905 A | 7/1975 | Albert |
| 4,156,047 A | 5/1979 | Wysong |
| 2006/0002965 A1* | 1/2006 | Hoeffkes .................. A61K 8/02 424/401 |
| 2006/0277693 A1* | 12/2006 | Saunier .................. A61K 8/494 8/405 |

FOREIGN PATENT DOCUMENTS

| | | |
|---|---|---|
| DE | 102004035348 A1 | 9/2005 |
| EP | 0493392 B1 | 3/1996 |
| EP | 1510529 A1 | 3/2005 |
| WO | 9101127 A1 | 2/1991 |
| WO | 02060980 A2 | 8/2002 |

OTHER PUBLICATIONS

EPO, International Search Report and Written Opinion issued in International Application No. PCT/EP2015/072830, dated Dec. 8, 2015.

* cited by examiner

*Primary Examiner* — Eisa B Elhilo
(74) *Attorney, Agent, or Firm* — Lorenz & Kopf, LLP

(57) ABSTRACT

Cosmetic compositions and methods for changing the color of keratinic fibers are provided herein. In an embodiment, a cosmetic composition for lightening the color of keratinic fibers includes at least two separately packaged formulations (A) and (B), which are mixed immediately prior to application to give an application mixture. The formulation (A) includes at least one dye chosen from the group of oxidation dye precursors, direct dyes, or a combination thereof. The composition (B) is a flowable composition including water and at least one oxidizing agent. Formulation (A) has been packaged in a water-soluble film including, based on its total weight, at least about 60% by weight of a polymer mixture having a multimodal molecular weight distribution.

20 Claims, No Drawings

COMPOSITIONS AND METHODS FOR COLORING KERATINIC FIBERS

CROSS-REFERENCE TO RELATED APPLICATION

This application is a U.S. National-Stage entry under 35 U.S.C. § 371 based on International Application No. PCT/EP2015/072830, filed Oct. 2, 2015, which was published under PCT Article 21(2) and which claims priority to German Application No. 102014223093.4, filed Nov. 12, 2014, which are all hereby incorporated in their entirety by reference.

TECHNICAL FIELD

The present disclosure relates to a cosmetic composition comprising a cosmetic formulation packaged in a water-soluble and/or water-dispersible casing and a method for coloring keratinic fibers.

BACKGROUND

In the field of decorative cosmetics, in particular cosmetics for the bleaching and the coloring of hair, there is a great demand for effective products that are both easy to handle and safe. Provided to the consumer by the field of hair cosmetics in particular are systems quite effective for hair lightening and coloring, but the improper use of them, for instance contact with areas of skin or the eyes, can lead to irritation and in extreme cases even to the triggering of allergies. There exists, therefore, a great demand for ensuring the safe handling of such cosmetic formulations in addition to putting an easily dispensed packaging system in the hands of the consumer, which also allows the necessary components to be mixed together or combined at the place of use. In this context, the avoidance of product dust is an important point, particularly in regard to bleaching or lightening hair cosmetics.

The literature contains initial attempts at solving the previously described technical problems. German Patent Application DE 10 2004 035 348 thus describes a hair coloring means comprising two formulations kept separate from one another, whereby one of these formulations is enclosed by a water-soluble packaging means.

European Patent EP 493 392 B1 discloses means for hair coloring and bleaching that are incorporated into polyvinyl alcohol packaging in order to reduce the irritation caused by powder dust.

European Patent Application EP 1 510 529 A1 describes the formulation of multimodal dispersions of vinyl alcohol/ninyl acetate copolymers.

Portion-sized cosmetic formulations disclosed in the prior art indeed offer improved handling and a reduction in the dust contamination coming from packaged cosmetic formulations, but the product portions packaged in water-soluble film systems pose the disadvantage of only slowly dissolving in water.

BRIEF SUMMARY

Cosmetic compositions and methods for changing the color of keratinic fibers are provided herein. In an embodiment, a cosmetic composition for lightening the color of keratinic fibers includes at least two separately packaged formulations (A) and (B), which are mixed immediately prior to application to give an application mixture. The formulation (A) includes at least one dye chosen from the group of oxidation dye precursors, direct dyes, or a combination thereof. The composition (B) is a flowable composition including water and at least one oxidizing agent. Formulation (A) has been packaged in a water-soluble film including, based on its total weight, at least about 60% by weight of a polymer mixture having a multimodal molecular weight distribution.

In another embodiment, a method for changing the color of keratinic fibers includes mixing at least two separately packaged formulations (A) and (B) immediately prior to application to give an application mixture. The formulation (A), packaged in a water-soluble film, is dissolved and incorporated into the formulation (B). The formulation (A) includes at least one dye chosen from the group of oxidation dye precursors, direct dyes, or a combination thereof. The formulation (B) is a flowable composition including water and at least one oxidizing agent. Formulation (A) has been packaged in a water-soluble film including, based on its total weight, at least about 60% by weight of a polymer mixture having a multimodal molecular weight distribution.

In another embodiment, a cosmetic composition for lightening the color of keratinic fibers includes at least two separately packaged formulations (A) and (B), which are mixed immediately prior to application to give an application mixture. The formulation (A) includes, based on its weight, from about 0.1 to about 10% by weight of at least one dye chosen from the group of oxidation dye precursors, direct dyes, or a combination thereof. The composition (B) is a flowable composition that includes water and at least one oxidizing agent. Formulation (B) includes, based on its weight, less than about 20% by weight fatty substances. The weight ratio of formulation (A) to formulation (B) is about 2:1 to about 1:100. Formulation (A) has been packaged in a water-soluble film including, based on its total weight, at least about 60% by weight of a polymer mixture having a multimodal molecular weight distribution. The polymer mixture has a polydispersity index of greater than about 2.2. The water-soluble film has a thickness from about 0.01 to about 0.1 mm.

DETAILED DESCRIPTION

The following detailed description is merely exemplary in nature and is not intended to limit the hair treatment agents and methods for treating hair. Furthermore, there is no intention to be bound by any theory presented in the preceding background or the following detailed description.

An object of the present disclosure is to provide portion-sized cosmetic formulations for bleaching keratinic fibers that are simple, safe and easy to handle, and the handling of which can take place, for example, without dust being generated while supplying the consumer an application mixture ready for use within a short period of time.

It has been found that the aforementioned problems can be solved by using special packaging. Said packaging not only avoids the generation of dust, but additionally enables the surprisingly quick and residue-free production of the cosmetic hair application mixture.

A first object of the present disclosure is a cosmetic composition for coloring keratinic fibers containing at least two separately packaged formulations (A) and (B), which are mixed immediately prior to application to give an application mixture, whereby the formulation (A) contains at least one dye from the group consisting of oxidation dye precursors and direct dyes, the formulation (B) is a flowable composition comprising water and at least one oxidizing agent, characterized in that the formulation (A) has been packaged in a water-soluble film consisting, based on its total weight, to an extent of at least about 60% by weight of a polymer mixture having a multimodal molecular weight distribution.

The molecular weight distribution of the polymer mixture contained in the water-soluble film is multimodal. In other words, the density of the molecular weight frequency distribution shows at least two modes (maxima), for example two, three, four, five or more modes. Particularly preferable is a bimodal molecular weight distribution because, as described above, on the one hand it has a beneficial effect on the product properties of the cosmetic composition as contemplated herein, and, on the other hand, it is easier to implement than a tri- or multi-modal frequency distribution.

The preferred bimodal molecular weight distribution can be symmetric or asymmetric.

In a preferred multimodal, preferably bimodal molecular weight distribution, the molecular weights of at least two of the maxima differ by from about 5% to about 120%, preferentially by from about 10% to about 90% and in particular from about 20% to about 60% based on the smallest identifiable modal molecular weight.

In a further preferred multimodal, preferably bimodal molecular weight distribution, the frequency of the minimum found between two maxima differs from the frequency of the smaller of these two maxima (the maximum with the lower frequency) by from about 5% to about 80%, preferably from about 10% to about 60% and in particular from about 20% to about 40%, each based on the frequency of the smaller of the two maxima.

In regard to the application properties of the composition as contemplated herein, in particular the quick and residue-free production of the cosmetic hair application mixture, it has been shown to be advantageous for the water-soluble film to consist of at least about 70% by weight, preferably of at least about 80% by weight, more preferably of at least about 90% by weight, and in particular of at least about 95% by weight of a polymer mixture having a multimodal molecular weight distribution. A bimodal molecular weight distribution is in turn preferential.

Advantageous in regard to product properties are polymer mixtures having a polydispersity index of greater than about 2.2, preferably greater than about 3.0, and in particular greater than about 4.6. In this context, polydispersity refers to the relationship between the weight average molecular weight and the number average molecular weight.

The weight average molecular weight (Mmit) is defined as Mmit=$\Sigma$ni Mi2/$\Sigma$ni Mi where Mmit=weight average molar mass, Ni=the number of macromolecules in the sample having exactly i repeating units and Mi=molecular weight i.

The weight average is obtained by methods taking into account the size and shape of a molecule in solution, for example static light scattering, small angle x-ray scattering, and sedimentation equilibrium measurements.

The number average molecular weight (Mn) is defined as Mn=$\Sigma$ni Mi2/$\Sigma$ni Mi where Mn=number average molar mass, ni=the number of macromolecules in the sample having exactly i repeating units and Mi=molecular weight i.

The number average can be determined using colligative methods such as cryoscopy and membrane or vapor pressure osmometry, and—as long as the number of end groups per molecule is known—by end-group analysis.

Water-soluble films not consisting entirely of the polymer mixture with the multimodal molecular weight distribution may contain additional active ingredients or fillers as well as solvents, in particular water, as additional ingredients.

Thus, included among the group of additional ingredients are, for example, components having a hair cosmetic effect as well as materials which protect the ingredients of formulation (A) enclosed in within the film material against decomposition or deactivation due to light irradiation. Antioxidants, UV absorbers and fluorescent dyes have proven to be particularly suitable in this regard.

Based on its total weight, the water-soluble film preferably has a water content of about 3.0 to about 12% by weight, more preferably from about 4.0 to about 10% by weight.

The thickness of the water-soluble film used for packaging formulation (A) preferably measures about 0.01 to about 0.1 mm, more preferably from about 0.01 to about 0.08 mm, and in particular from about 0.02 to about 0.06 mm.

The water-soluble film within which formulation (A) is packed may comprise one or more structurally varying water-soluble polymers. Particularly suitable as water-soluble polymer(s) are polymers from the group consisting of (optionally acetalyzed) polyvinyl alcohols (PVAL), polyvinylpyrrolidone, polyethylene oxide, gelatin and cellulose.

In a first preferential embodiment, the polymer mixture with the multimodal and preferably bimodal molecular weight distribution comprises to two vinyl acetate/vinyl alcohol copolymers. Therefore, the preferential cosmetic compositions are characterized by the polymer mixture consisting, based on its total weight, of a mixture comprising at least about 60% by weight, preferably at least about 80% by weight, more preferably at least about 90% by weight, quite preferably at least about 95% by weight a1) water-soluble vinyl alcohol/ninyl acetate copolymer a1) and a2) at least one water-soluble vinyl alcohol/vinyl acetate copolymer a2) different from the water-soluble vinyl alcohol/ninyl acetate copolymer a1).

In the aforementioned preferential embodiment based on two water-soluble vinyl alcohol/ninyl acetate copolymers, the polymer mixture preferably has a polydispersity index greater than about 2.2, more preferably greater than about 3.0, and in particular greater than about 4.6, whereas the polydispersity index of the vinyl alcohol/ninyl acetate copolymer a1) is preferably between about 1.8 and about 2.3.

Particularly advantageous product properties are to be achieved using vinyl alcohol/vinyl acetate copolymers a1) having a degree of hydrolysis between about 84% and about 90%, preferably between about 85% and about 89%, and in particular between about 86% and about 88%. In other words, the corresponding copolymers a1) exhibit a residual content of acetyl groups of between about 10% and about 16%, preferably of between about 11% and about 15%, and in particular of between about 12% and about 14%.

In addition to the polydispersity index and the degree of hydrolysis, the viscosity of aqueous solutions of the vinyl alcohol/ninyl acetate has also proven to be a distinguishing feature of particularly advantageous copolymers. Therefore, preferred cosmetic compositions are characterized in that the vinyl alcohol/vinyl acetate copolymer a1) has a viscosity (20° C., 4% by weight solution in water, measured using a Brookfield LV Viscosimeter with UL adapter) of between about 12 cP and about 20 cP, preferably of between about 14 cP and about 19 cP, and in particular of between about 16 cP and about 18 cP.

In comparison, the vinyl alcohol/ninyl acetate copolymer a2) (20° C., 4% by weight solution in water, measured using a Brookfield LV Viscosimeter with UL adapter) preferably has a viscosity of between about 20 cP and about 30 cP, preferably of between about 20 cP and about 28 cP, and in particular of between about 20 cP and about 25 cP.

In addition to the previously described combination of two vinyl alcohol/vinyl acetate copolymers, additional preferable polymer combinations exist having properties advantageous with regard to the aforementioned technical functions. In an alternative preferential embodiment of the cosmetic compositions as contemplated herein, the polymer mixture consists, based on its total weight, of a mixture comprising at least about 60% by weight, hence preferably at least about 80% by weight, more preferably at least about 90% by weight, and particularly preferably at least about 95% by weight a1) water-soluble vinyl alcohol/ninyl acetate copolymer a1) and a2) at least one optionally modified water-soluble polysaccharide, preferably at least one water-soluble polysaccharide from the group consisting of methyl cellulose, carboxymethyl cellulose, ethyl cellulose, hydroxyethyl cellulose, hydroxypropyl cellulose, hydroxypropyl methylcellulose, dextrin, and hydroxypropyl starch, particularly preferably at least one water-soluble polysaccharide from the group of hydroxypropyl starches.

On the other hand, the polydispersity index of the aforementioned polymer mixtures of vinyl alcohol/vinyl acetate copolymers and polysaccharide is preferably greater than about 2.2, more preferably greater than about 3.0, and in particular greater than about 4.6, whereas the polydispersity index of the vinyl alcohol/ninyl acetate copolymer a1) in these mixtures is preferably between about 1.8 and about 2.3.

If the vinyl alcohol/ninyl acetate copolymer a1) is combined with a polysaccharide, then the vinyl alcohol/ninyl acetate copolymer a1) exhibits a degree of hydrolysis between about 84% and about 90%, preferably between about 85% and about 89%, and in particular between about 86% and about 88%. The viscosity of the vinyl alcohol/ninyl acetate copolymer a1) (20° C., 4% by weight solution in water, measured using a Brookfield LV Viscosimeter with UL adapter) is preferably between about 12 cP and about 20 cP, more preferably between about 14 cP and about 19 cP, and in particular between about 16 cP and about 18 cP.

In addition to the water-soluble films described above, the cosmetic compositions as contemplated herein comprise the formulations (A) and (B). In regard to the dissolution behavior and functional behavior of said compositions, it has proven advantageous for the weight ratio of formulation (A) to formulation (B) to be about 2:1 to about 1:100, preferably about 2:1 to about 1:10, and in particular about 2:1 to about 1:3.

Formulation (A) contains as a distinguishing component at least one colorant from the group consisting of oxidation dye precursors and direct dyes. The proportion by weight of the oxidation dye precursors and the direct dyes preferably consists of from about 0.1 to about 10% by weight, preferably about 0.2 to about 8.0% by weight, and in particular from about 0.5 to about 6.0% by weight based on the total weight of formulation (A).

In a first advantageous embodiment, the formulation (A) contains at least one oxidative dye (oxidation dye precursor). In terms of the present disclosure, oxidative dyes are understood to be means for changing hair color that cause the lasting coloration of the fibers by oxidizing the oxidation dye precursors. Included within the term "oxidation dye precursor" are so-called developer components and coupler components. Under the influence of oxidation agents or atmospheric oxygen, the developer components form the actual dyes together with one another or by coupling with one or more coupling components. Oxidation dyes are distinguished by excellent and long-lasting coloring results. Achieving bioanalogous colorations normally requires using a mixture of a large number of oxidation dye precursors; in many cases, direct dyes are additionally used for shading.

The present disclosure does not present any restrictions with respect to the dye precursors usable in the formulation (A) as contemplated herein. As dye precursors, the formulation (A) as contemplated herein (A) may contain oxidation dye precursors of the developer and/or the coupler type and precursors of bioanalogous dyes such as indole and indoline derivatives as well as mixtures made from representatives of these groups.

Within the scope of a first preferred embodiment of the present disclosure, the formulation (A) as contemplated herein contains at least one oxidation dye precursor of the developer type and/or the coupler type.

It may be preferable in terms of the present disclosure to use a p-phenylenediamine derivative or a physiologically compatible salt thereof as the developer component. Particularly preferable p-phenylenediamines are chosen from among p-phenylenediamine, p-tolylenediamine, 2-chloro-p-phenylenediamine, N,N-bis-(2-hydroxyethyl)-p-phenylenediamine, N-phenyl-p-phenylenediamine, 2-(2-hydroxyethyl)-p-phenylenediamine, N-(4-amino-3-methylphenyl)-N-[3-(1H-imidazole-1-yl)propyl]amine, as well as their physiologically compatible salts. Particularly preferable cosmetic compositions are characterized in that formulation (A) contains at least one oxidation dye precursor of the developer type, preferably at least one compound from the group consisting of p-toluenediamine, 2-(2-hydroxyethyl)-p-phenylenediamine, N,N-bis-(2-hydroxyethyl)-p-phenylenediamine, 2-methoxymethyl-p-phenylenediamine and/or their physiologically compatible salts.

Used as developer components in a further preferable embodiment are compounds containing at least two aromatic nuclei which are substituted with amino and/or hydroxyl groups. Preferable binuclear developer components in particular are: N,N'-bis-(2-hydroxyethyl)-N,N'-bis-(4'-aminophenyl)-1,3-diamino-propan-2-ol and bis-(2-hydroxy-5-aminophenyl)-methane, and their physiologically compatible salts.

It may furthermore be preferable in terms of the present disclosure to use a p-aminophenol derivative or a physiologically compatible salt thereof as the developer component. Preferable p-aminophenols in particular are p-aminophenol, N-methyl-p-aminophenol, and 4-amino-3-methylphenol and their physiologically compatible salts. The developer component may further be selected from among o-aminophenol and derivatives thereof, for example 2-amino-5-methylphenol and physiologically compatible salts thereof. Particularly preferable cosmetic compositions are characterized in that formulation (A) contains at least one oxidation dye precursor of the developer type, preferably at least one compound selected from the group consisting of bis-(2-hydroxy-5-aminophenyl)methane, p-aminophezol, 4- and amino-3-methylphenol and/or their physiologically compatible salts.

Finally, the developer component may also be made of heterocyclic developer components, for example selected from derivatives of pyridine, pyrimidine, pyrazole or pyrazolopyrimidine and their physiologically compatible salts. Preferable pyrimidine derivatives are in particular 2,4,5,6-tetraaminopyrimidine and 4-hydroxy-2,5,6-triaminopyrimidine and their physiologically compatible salts. One preferable pyrazole derivative is 4,5-diamino-1-(2-hydroxyethyl)-pyrazole and physiologically compatible salts thereof. Particularly preferable cosmetic compositions are characterized in that formulation (A) contains at least one oxidation dye precursor of the developer type, preferably at least one compound from the group consisting of 4,5-diamino-1-(2-hydroxyethyl)pyrazole, 2,4,5,6-tetraaminopyrimidine, 4-hydroxy-2,5,6-triaminopyrimidine and/or their physiologically compatible salts.

In a further preferred embodiment, the compositions B contain at least one coupler component.

Normally used as coupler components are phenylenediamine derivatives, naphthols, resorcinol and resorcinol derivatives, pyrazolone and m-aminophenol derivatives. Particularly suitable coupler substances are 1-naphthol, 1,5- and 2,7-dihydroxynaphthalene, 1-acetoxy-2-methoxynaphthalene, resorcinol, 4-chloro-resorcinol and 2-amino-3-hydroxypyridine and their physiologically compatible salts.

Coupler components preferable in terms of the present disclosure are
(A) m-aminophenol and derivatives thereof such as 5-amino-2-methylphenol, 3-amino-2-chloro-6-methylphenol, 5-amino-4-chloro-2-methylphenol, 5-(2'-hydroxyethyl)-amino-2-methyl phenol, and 2,4-dichloro-3-aminophenol,
(B) o-aminophenol and derivatives thereof, for example 2-amino-5-methylphenol,
(C) m-diaminobenzene and derivatives thereof such as 2,4-diaminophenoxyethanol, 1,3-bis-(2',4'-diaminophenoxy)-propane, 1-methoxy-2-amino-4-(2'-hydroxyethylamino)benzene, 2,6-bis-(2'-hydroxyethylamino)-1-methylbenzene, 2-({3-[(2-hydroxyethyl)amino]-4-methoxy-5-methylphenyl}amino)ethanol and 2-({3-[(2-hydroxyethyl)amino]-2-methoxy-5-methylphenyl}amino)ethanol,
(D) o-diaminobenzene and derivatives thereof,
(E) di- or trihydroxybenzene derivatives such as 2-methylresorcinol and 1,2,4-trihydroxybenzene,
(F) pyridine derivatives such as 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine,
(G) naphthaline derivatives such as 1-naphthol and 2-methyl-1-naphthol,
(H) morpholine derivatives such as 6-hydroxybenzomorpholine,
(I) quinoxaline derivatives,
(J) pyrazole derivatives such as 1-phenyl-3-methylpyrazole-5-on,
(K) indole derivatives such as 6-hydroxyindole,
(L) pyrimidine derivatives or
(M) methylenedioxybenzene derivatives such as 1-(2'-hydroxyethyl)-amino-3,4-methylenedioxybenzene
as well as their physiologically compatible salts.

Particularly preferable alternative cosmetic compositions are characterized in that formulation (A)
contains at least one oxidation dye precursor of the coupler type, preferably at least one compound from the group consisting of 3-aminophenol, 5-amino-2-methylphenol, 3-amino-2-chloro-6-methylphenol, 2,4-dichloro-3-aminophenol and/or their physiologically compatible salts.
contains at least one compound from the group 2-(2,4-diaminophenoxy)ethanol, 1,3-bis(2,4-di-aminophenoxy)propane, 1-methoxy-2-amino-4-(2-hydroxyethylamino)benzene, 2,6-bis(2'-hydroxyethylamino)-1-methylbenzene and/or their physiologically compatible salts;
contains at least one compound from the group consisting of resorcinol, 2-methylresorcinol, and 4-chlororesorcinol;
contains at least one compound from the group consisting of 2-amino-3-hydroxypyridine, 3-amino-2-methylamino-6-methoxypyridine, 2,6-dihydroxy-3,4-dimethylpyridine and/or their physiologically compatible salts;
contains at least one compound from the group consisting of 2-naphthol and 2,7-dihydroxynaphthalene.

Quite particularly preferable coupler components in terms of the present disclosure are 1-naphthol, 1,5- and 2,7-dihydroxynaphthalene, 5-amino-2-methylphenol, 2-amino-3-hydroxypyridine, resorcinol, 4-chlororesorcinol, 2-methylresorcinol and 2,6-dihydroxy-3,4-dimethylpyridine and their physiologically compatible salts.

The formulation (A) contains both the developer components and the coupler components in a preferable quantity about 0.1 to about 5.0% by weight, preferably about 0.2 to about 5.0% by weight, and in particular from about 0.5 to about 5.0% by weight, each based on the total weight of the formulation (A). Developer components and coupler components are, in this context, generally used in approximately molar quantities with respect to one another. Although molar utilization has proven useful, a certain excess of individual oxidation dye precursors is not disadvantageous, so developer components and coupler components can be contained at a molar ratio of from about 1:0.5 to about 1:3, in particular from about 1:1 to about 1:2.

In a further embodiment of the present disclosure, the formulation (A) includes at least one precursor of a bioanalagous dye as an oxidation dye precursor. Precursors of bioanalogous dyes preferable for use are those indoles and indolines comprising least one hydroxy or amino group, preferably as a substituent on a six-membered ring. Particularly preferable derivatives of indolines are 5,6-dihydroxyindoline and 2,3-dioxoindoline (isatin) and their physiologically compatible salts. A particularly preferable indole derivative is 5,6-dihydroxyindole and its physiologically compatible salts.

In addition to oxidation dye precursors or as an alternative to these dyes, the formulation (A) may also contain direct dyes. In a further preferred embodiment, the formulation (A) contains at least one direct dye. Direct dyes can be divided into anionic, cationic and nonionic direct dyes. The direct dyes are preferably selected from among the nitrophenylenediamines, the nitroaminophenols, the azo dyes, the anthraquinones or the indophenols and their physiologically compatible salts.

Particularly suitable as anionic direct dyes are 2,4-dinitro-1-naphthol-7-sulfonic acid disodium salt (C.I. 10.316; Acid Yellow 1; Food Yellow No. (1), 2-(indan-1,3-dion-2-yl)chinolin-x,x-sulfonic acid (mixture of mono- and disulfonic acid (C.I. 47.005;) D & C Yellow No. 10; Food Yellow No. 13; Acid Yellow 3, Yellow 10), 5-Hydroxy-1-(4-sulfophenyl)-4-[(4-sulfophenyl)-azo]pyrazol-3-carboxylic acid trisodium salt (C.I. 19.140; Food Yellow No. 4; Acid Yellow 23), 3-[(4-phenylamino)phenyl]azobezolsulfonic acid sodium salt (C.I. 13.065; Ki406; Acid Yellow 36), 4-[(2-hydroxynaphth-1-yl)azo]-benzenesulfonic acid sodium salt (C.I. 15.510; Acid Orange 7), 6-hydroxy-5-[(4-sulfonaphth-1-yl)azo]-2,4-naphthalenedisulfonic acid trisodium salt (C.I.16.255; Ponceau 4R; Acid Red 18), 8-amino-1-hydroxy-2-(phenylazo)-3,6-naphthalene-disulfonic acid trisodium salt (C.I. 17.200; Acid Red 33; Red 33), N[6-(diethylamino)-9-(2,4-disulfophenyl)-3H-xanthen-3-yliden]-N-ethylethanammonium hydroxide, inner salt, sodium salt (C.I. 45.100; Acid Red 52),2',4',5',7'-tetrabromo-4,5,6,7-tetrachloro-3', 6'-dihydroxyspiro[isobenzofuran-1(3H),9'9H] xanthen]-3-on-disodium salt (C.I. 45.410; Acid Red 92), 3-hydroxy-4-[(4-methyl-2-sulfonphenyl)azo]-2-naphthalenecarboxylic acid-calcium salt (C.I. 15.850: 1; Pigment Red 57:1) 1,4-bis[(2-sulfo-4-methylphenyl)amino]-9,10-anthraquinone-disodium salt (C.I. 61.570; Acid Green 25), bis[4-(dimethylamino)phenyl]-(3,7-disulfo-2-hydroxynaphth-1-yl)carbenium inner salt, sodium salt (C.I. 44.090; Food Green No. 4; Acid Green 50), N-[4-[(2,4-disulfophenyl)[4-[ethyl(phenylmethyl)amino)phenyl]methylene]-2,5-cyclohexadien-1-yliden]-N-ethylbenzolmethanaminium-hydroxide, inner salt, sodium salt (C.I. 42.080; Acid Blue 7), (2-sulfophenyl)di[4-(ethyl((4-sulfophenyl)methyl)amino) phenyl]-carbenium disodium salt, betaine (C.I. 42.090; Acid Blue 9; FD&C Blue No. 1), 1-amino-4-(cyclohexylamino)-9,10-anthraquinone-2-sulfonic acid sodium salt (C.I. 62.045; Acid Blue 62), 1-hydroxy-4-[(4-methyl-2-sulfophenyl)amino]-9,10-anthraquinone-sodium salt (C.I. 60.730; D&C Violet No. 2; Acid Violet 43), 5-amino-4-hydroxy-6-[(4-nitrophenyl)-azo]-3-(phenylazo)-2,7-naphthalene-disulfonic acid disodium salt (C.I. 20.470; Acid Black 1), 3-hydroxy-4-[(2-hydroxynaphth-1-yl)azo]-7-nitro-1-naphthalene-sulfonic acid chromium complex (3:2 (C.I. 15.711; Acid Black 52), 3',3",4,5,5',5",6,7-Octabromophenolsulfonphthalein (tetrabromophenol blue).

Preferable anionic direct dyes are the compounds known by the international designations or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Particularly suitable as cationic direct dyes are di[4-(diethylamino)phenyl][4-(ethylamino)naphthyl]carbenium chloride (C.I. 42.595; Basic Blue 7), di[4-(dimethylamino) phenyl][4-(phenylamino)naphthyl] carbenium chloride (C.I. 44.045; Basic Blue 26), 8-amino-2-bromo-5-hydroxy-4-imino-6-[(3-(trimethylammonio)phenyl)amino]-1(4H)-naphthalinone chloride (C.I. 56.059; Basic Blue No. (99), tri(4-amino-3-methylphenyl)carbenium chloride (C.I. 42.520; Basic Violet 2), di(4-aminophenyl)(4-amino-3-methylphenyl)carbenium chloride (C.I. 42.510 Basic Violet 14), 1-[(4-aminophenyl)azo]-7-(trimethylammonio)-2-naphthol chloride (C.I. 12.250; Basic Brown 16), 1-[(4-amino-3-nitrophenyl)azo]-7-(trimethylammonio)-2-naphthol chloride (C.I. 12.251; Basic Brown 17), 3-[(4-amino-2,5-dimethoxyphenyl)azo]-N,N,N-trimethylbenzolaminium chloride (C.I. 12.605, Basic Orange 69), 2-[((4-dimethylamino)phenyl)azo]-1,3-dimethyl-1H-imidazolium chloride (Basic Red 51), 2-hydroxy-1-[(2-methoxyphenyl)azo]-7-(trimethylammonio)-naphthalene chloride (C.I. 12.245; Basic Red 76), 2-[4-aminophenyl]azo]-1,3-dimethyl -1H-imidazolium chloride (Basic Orange 31), 3-methyl-1-phenyl-4-[(3-(trimethylammonio)phenyl)azepyrazol-5-on-chloride (C.I. 12.719; Basic Yellow 57), 1-methyl-4-((methylphenylhydrazono)methyl)-pyridinium-methyl sulfate (Basic Yellow 87), 1-(2-morpholiniumpropylamino)-4-hydroxy-9,10-anthraquinone methyl sulfate, 4-formyl-1-methylquinolonium-p-toluenesulfonate and direct dyes containing a heterocycle comprising at least one quaternary nitrogen atom.

Particularly suitable as nonionic direct dyes in particular are nonionic nitro dyes, chinon dyes, and neutral azo dyes.

Suitable blue nitro dyes in particular are 1,4-bis[(2-hydroxyethyl)amino]-2-nitrobenzene (HC Violet BS), 1-(2-hydroxyethyl)amino-2-nitro-4-[di(2-hydroxyethyl)amino]-benzene (HC Blue 2), 4-[di(2-hydroxyethyl)amino]-1-[(2-methoxyethyl)amino]-2-nitrobenzene (HC Blue 11), 4-[ethyl-(2-hydroxyethyl)-amino]-1-[(2-hydroxyethyl) amino]-2-nitrobenzol-hydrochloride (HO Blue 12), 1-(2-hydroxyethyl)amino-2-nitro-4-N-ethyl-N-(2-hydroxyethyl) aminobenzol (HC Blue 15), 1-amino-3-methyl-4-[(2-hydroxyethyl)amino)]-6-nitrobenzene (HC Violet 1), 1-(3-hydroxypropylamino)-4-[di(2-hydroxyethyl)amino]-2-nitrobenzene (HC Violet 2).

Suitable nitro dyes in particular are 1-amino-4[(2-hydroxyethyl)amino]-2-nitrobenzene (HC Red 7), 2-amino-4, 6-dinitrophenol (picramic acid) and their salts, 1,4-diamino-2-nitrobenzene (C.I. 76.070), 4-amino-2-nitro-diphenylamine (HC Red 1), 1-amino-4-di(2-hydroxyethyl) amino]-2-nitrobenzene-hydrochloride (HC Red 13), 1-amino-4-[di(2-hydroxyethyl)-amino]-5-chloro-2-nitrobenzene, 4-amino-1-[(2-hydroxyethyl)amino]-2-nitrobenzene (HC Red 3), 4-[(2-hydroxyethyl)-amino]-3-nitrotoluene, 4-amino-3-nitrophenol, 4-[(2-hydroxyethyl)-amino] -3-nitrophenol, 4-[(2-nitrophenyl)amino]phenol (HC Orange 1), 1-[(2-aminoethyl)amino]-4-(2-hydroxyethoxy)-2-nitrobenzene (HC Orange 2), 1-amino-5-chloro-4-[(2,3-dihydroxypropyl)amino]-2-nitrobenzene (HC Red 10), 5-chloro-1,4-[(2,3-dihydroxypropyl)amino]-2-nitrobenzene (HC Red 11), 2-[(2-hydroxyethyl)amino]-4,6-dinitrophenol and salts thereof, 4-ethylamino-3-nitrobenzoic acid, 2-[(4-amino-2-nitrophenyl)amino]-benzoic acid, 2-chloro-6-ethylamino-4-nitrophenol, 2-amino-6-chloro-4-nitrophenol, 4-[(3-hydroxypropyl)amino]-3-nitrophenol (HC Red BN), 1,2,3,4-tetrahydro-6-nitrochinoxalin, 6-hydroxy-5-((2-methoxy-5-methyl-4-sulfophenyl)azo)-2-naphthalenesulfonic acid (Curry Red).

Suitable yellow nitro dyes in particular are 1,2-diamino-4-nitrobenzene (C.I. 76.020), 1-[(2-hydroxyethyl)amino]-2-nitrobenzene (HC Yellow 2), 1-(2-hydroxyethoxy)-2-[(2-hydroxyethyl)amino]-5-nitrobenzene (HC Yellow 4), 1-amino-2-[(2-hydroxyethyl)amino]-5-nitrobenzene (HC Yellow 5), 4-[(2,3-dihydroxypropyl)-amino]-3-nitro-1-trifluormethylbenzene (HC Yellow 6), 2-[(2-hydroxyethyl) amino]-1-methoxy-5-nitrobenzene, 2-amino-4-nitrophenol, 1-(2-hydroxyethoxy)-3-methylamino-4-nitrobenzene, 2,3-(dihydroxypropoxy)-3-methylamino-4-nitrobenzene, 3-[(2-aminoethyl)amino]-1-methoxy-4-nitrobenzene-hydrochloride (HC Yellow 9), 1-chloro-2,4-bis[(2-hydroxyethyl) amino]-5-nitrobenzene (HC Yellow 10), 2-[(2-hydroxyethyl)amino]-5-nitrophenol (HC Yellow 11), 1-[(2'-ureidoethyl)amino]-4-nitrobenzene, 1-amino-4-[(2-aminoethyl)amino]-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow 12), 4-[(2-hydroxyethyl)amino]-3-nitro-1-trifluormethylbenzene (HC Yellow 13).

Suitable chinon dyes in particular are 1-[(2-hydroxyethyl) amino]-4-methylamino-9,10-anthraquinone (C.I. 61.505, Disperse Blue 3), mixtures of 1,4-bis[(2-hydroxyethyl) amino]anthra-9,10-guinone having 1-[(2-hydroxyethyl) amino]-4-[(3-hydroxypropyl)amino]anthra-9,10-guinone and 1,4-bis[(3-hydroxypropyl)amino]anthra-9,10-guinone (Disperse Blue 377), 1,4-diamino-9,10-anthrachinon (C.I. 61.100, Disperse Violet 1), 1-amino-4-(methylamino)-9,10-anthraquinone (C.I. 61.105, Disperse Violet 4, Solvent Violet No. 12), 2-hydroxy-1,4-naphthoquinone (Lawsone, C.I. 75.480, Natural Orange 6), 1,4-bis[(2,3-dihydroxypropyl) amino]-9,10-anthracenedione (HC Blue 14).

Suitable neutral azo dyes in particular are 1-[di(2-hydroxyethyl)amino]-3-methyl-4-[(4-nitrophenyl)azo]-benzene (C.I. 11.210, Disperse Red 17), 1-[di(2-hydroxyethyl)amino]-4-[(4-nitrophenyl)azo]-benzene (Disperse Black 9), 4-[(4-aminophenyl)azo]-1-[di(2-hydroxyethyl)amino]-3-methylbenzene (HC Yellow 7), 2,6-diamino-3-[(pyridine-3-yl)azepyridine, 4-[(4-nitrophenyl)azo]-aniline (C.I. 11.005; Disperse Orange 3).

The formulation (A) preferably exists in solid form, for example in the form of a powder, a granulate or a compressed body, for example in the form of a tablet. Preferential cosmetic formulations (A) exist in powder form.

Prior to being applied to the hair, the formulation (A) is preferably mixed with and dissolved in the aqueous formulation (B). A distinguishing component of the aqueous formulation (B) is at least one oxidizer. In a preferred embodiment, the formulation (B) is an aqueous solution of hydrogen peroxide. Preferable is a formulation (B), which, based on its weight, contains about 50 to about 98% by weight, preferably about 60 to about 95% by weight, more preferably about 70 to about 88% by weight water, and, calculated as 100% H2O2, contains about 0.5 to about 20% by weight, preferably about 1 to about 15% by weight, and particularly preferably about 2 to about 12% by weight hydrogen peroxide.

As an additional component, the formulation (B) preferably contains emulsifiers or surface-active agents.

Preferred as a first group are the anionic surfactants. In terms of the present disclosure, anionic surfactants are all anionic surface-active substances suitable for use on the human body. Such substances are characterized by a water-solubilizing anionic group such as, for example, a carboxylate, sulfate, sulfonate or phosphate group and a lipophilic alkyl group comprising around 8 to 30 carbon atoms. In addition, glycol or polyglycol ether groups and ester, ether and amide groups as well as hydroxyl groups may also be present in the molecule. Examples of such anionic surfactants, each in the form of the sodium, potassium and ammonium salts as well as the mono-, di- and trialkanolammonium salts comprising 2 to 4 carbon atoms in the alkanol group, are linear and branched fatty acids comprising 8 to 30 carbon atoms (soaps); ether carboxylic acids, in particular of the formula $RO(CH_2CH_2O)_xCH_2COOH$, in which R is a linear alkyl group comprising 8 to 30 carbon atoms and x=0 or from 1 to 16; acyl sarcosides; acyl taurides; acyl isethionates; sulfosuccinic acid mono- and dialkylesters as well as sulfosuccinic acid monoalkyl polyoxyethyl esters; linear alkane sulfonates; linear α-olefin sulfonates; sulfonates of unsaturated fatty acids; α-sulfofatty acid methyl esters of fatty acids; alkyl sulfates and alkyl ether sulfates, in particular of the formula $RO(CH_2CH_2O)_xSO_3H$, in which R stands for a linear alkyl group comprising 8 to 30 carbon atoms and x stands for 0 or a number from 1 to 12; mixtures of surface-active hydroxysulfonates; sulfated hydroxyalkyl polyethylene- and/or hydroxyalkylene propylene glycol ethers; esters of tartaric acid and citric acid with alcohols; alkyl- or alkenyl ether phosphates of the formula $RO(C_2H_4O)_xP(=O)(OH)(OR')$ where R is an aliphatic, optionally hydrocarbon residue comprising 8 to 30 carbon atoms, R' is hydrogen, a residue $(CH_2CH_2O)_yR$ and x and y are independent of one other and stand for a number from 1 to 10; sulfated fatty acid alkylene glycol esters of the formula $RC(O)O(alkO)_nSO_3H$ in which R is a linear or branched, aliphatic, saturated and/or unsaturated alkyl residue comprising from 6 to 22 carbon atoms, alk is $CH_2CH_2$, $CHCH_3CH_2$ and/or $CH_2CHCH_3$ and n is a number from 0.5 to 5; as well as monoglyceride sulfates and monoglyceride ether sulfates.

Particularly preferable cosmetic compositions in terms of the present disclosure are characterized in that they additionally contain at least one anionic surfactant. Preferable anionic surfactants are fatty acids, alkyl sulfates, alkyl ether sulfates and ether carboxylic acids comprising 10 to 20 carbon atoms in the alkyl group and up to 16 glycol ether groups in the molecule. Particularly preferable are C8C20-alkyl sulfates, in particular sodium cetearyl sulfate and sodium lauryl sulfates as well as C8C20-alkyl ether sulfates comprising from 2 to 12, preferably from 2 to 4 ethylene oxide groups, in particular sodium lauryl ether sulfate (INCI: Sodium Laureth Sulfate). The proportion by weight of the anionic surfactant preferably consists of from about 0.1 to about 8.0% by weight, preferably from about 0.1 to about 4.0% by weight, and in particular from about 0.1 to about 2.0% by weight based on the total weight of the formulation (B).

Furthermore, preferred emulsifiers are PEG derivatives of hydrogenated castor oil, for example available under the name PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil or PEG-40 Hydrogenated Castor Oil. The use of PEG-40 Hydrogenated Castor Oil is preferable in terms of the present disclosure. It is preferably contained in a quantity from about 0.05 to about 1.5% by weight, preferably from about 0.1 to about 1.0% by weight, likewise preferably from about 0.2 to about 0.8% by weight or from about 0.3 to about 0.6% by weight.

In order to enable the application mixture made from formulation (A) and (B) to be applied cleanly and to a restricted area, it has proved to be advantageous for the composition to have an increased viscosity. It is advantageous in this regard if the composition is not present as a paste, viscous cream or thickened gel, but rather possesses sufficient flowability. Furthermore, once made ready for use, the composition must possess rheological properties allowing it to be applied to the fibers to be bleached while at the same time keeping the composition from running or flowing away from the place of action during the period of application. Therefore, the application mixtures preferably have a viscosity of from about 5 to about 100 Pa·s, preferably from about 10 to about 50 Pa·s, in particular from about 10 to about 20 Pa·s, and particularly preferably from about 10 to about 16 Pa·s (Brookfield, 22° C., #5 spindle, 4 rpm). For this purpose, preferable formulations (B) contain at least one thickening agent and/or at least one gelling agent. Corresponding methods as contemplated herein in which the formulation (B) additionally contains at least one thickening agent and/or at least one gelling agent are preferable in terms of the present disclosure. Inorganic as well as organic substances are suitable as thickening agents or gelling agents.

The thickening agent can, for example, be selected from among the following polymeric thickening agents known by their INCI names: Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, AcrylatesNinyl Isodecanoate Crosspolymer, Acrylic Acid/Acrylonitrogens Copolymer, Agar, Agarose, Alcaligenes Polysaccharides, Algin, Alginic Acid, Ammonium Acrylates/Acrylonitrogens Copolymer, Ammonium Acrylates Copolymer, Ammonium AcryloyldimethyltaurateNinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, Astragalus Gummifer Gum, Attapulgite, *Avena Sativa* (Oat) Kernel Flour, Bentonite, Butoxy Chitosan, Caesalpinia Spinosa Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Cholesteryl Hexyl Dicarbamate Pullulan, *Cyamopsis Tetragonoloba* (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, *Glycine Soja* (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxystearamide MEA, Isobutylene/Sodium Maleate Copolymer, Lithium Magnesium Silicate, Lithium Magnesium Sodium Silicate, *Macrocystis Pyrifera* (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium AcrylatesNinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, *Solanum Tuberosum* (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, *Triticum Vulgare* (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, *Zea Mays* (Corn) Starch.

Particularly preferable are polymeric thickeners chosen from among polymeric, anionic, ampiphilic thickeners, most preferably those with the INCI names Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-20 Acrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylates/Steareth-20 Methacrylate Crosspolymer.

The polymeric thickening agents are preferably contained in the formulation (B) in a quantity about 0.5 to about 20% by weight, in particular from about 0.5 to about 10% by weight.

It has proven to be particularly advantageous to adjust the viscosity of the application mixture obtained from mixing the formulations (A) and (B) by selecting a suitable polymer mixture for the water-soluble film. Thus, the viscosity of the application mixture, the application properties thereof, and the bleaching action can be advantageously influenced by both the chemical nature of the polymer mixture and by the quantity of the polymer mixture used for the packaging. Therefore, preferable cosmetic compositions are characterized in that the proportion by weight of the polymer mixture with the multimodal molecular weight distribution is about 1 to about 15% by weight, preferably about 2 to about 10% by weight, and in particular is about 3 to about 8% by weight of the total weight of the formulations (A) and (B), including the water-soluble film.

Furthermore, the formulation (B) may contain additional active ingredients, auxiliaries and additives, such as nonionic polymers, for example vinylpyrrolidone/vinyl acrylate copolymers, polyvinylpyrrolidone and vinylpyrrolidone/vinyl acetate copolymers and polysiloxanes, cationic polymers, for example quaternized cellulose ethers, polysiloxanes having quaternary groups, dimethyldiallylammonium chloride polymers, acrylamide/dimethyl diallyl ammonium chloride copolymers, dimethylaminoethylmethacrylate/vinylpyrrolidone copolymers quaternized with diethyl sulfate, vinylpyrrolidone/imidazolinium methochloride copolymers, and quaternized polyvinyl alcohol, zwitterionic and amphoteric polymers, for example, acrylamidopropyl-tri-methyl ammonium chloride/acrylate copolymers and octylacrylamide/methyl methacrylate/tert-butylaminoethyl methacrylate/2-hydroxypropyl methacrylate copolymers, anionic polymers, for example polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic acid anhydride copolymers, and acrylic acid/ethyl acrylate/N-tert.butyl-acrylamide terpolymers, solvents and solubilizers such as ethanol, isopropanol, ethylene glycol, propylene glycol, glycerin and diethylene glycol, consistency enhancers such as sugar esters, polyolesters or polyol alkyl ethers, stabilizing agents for hydrogen peroxide, for example complexing agents such as EDTA, NTA, 3-alaninediacetic acid, and phosphonic acids.

Regarding the application properties of the cosmetic composition as contemplated herein, it has proven advantageous to reduce the proportion by weight of hydrophobic components in the formulation (B) as much as possible. Therefore, preferable cosmetic compositions are characterized in that, based on its weight, formulation (B) contains less than about 20% by weight, preferably less than about 10% by weight, and in particular less than about 5.0% by weight fatty substances. In terms of the present disclosure, fatty substances include those compounds less than 1 g of which can dissolve in 100 g of water at 20° C. Include among these are, for example, waxes such as candelilla wax, carnauba wax or beeswax, shea butter, coconut oil, C12 to C20- fatty acids (in particular palmitic acid, stearic acid), silicones and paraffins.

As initially stated, cosmetic compositions as contemplated herein are particularly suitable for the production of hair bleaching compositions. Therefore, a further object as contemplated herein is a method for changing the color of keratinic fibers in which at least two separately packaged formulations (A) and (B) are mixed immediately prior to application to give an application mixture, and in which the formulation (A) packaged in a water-soluble film is dissolved and incorporated into the formulation (B), whereby the formulation (A) includes at least one dye chosen from the group of oxidation dye precursors, direct dyes, or a combination thereof the formulation (B) is a flowable composition comprising water and at least one oxidizing agent, characterized in that the formulation (A) has been packaged in a water-soluble film consisting, based on its total weight, to an extent of at least about 60% by weight of a polymer mixture having a multimodal molecular weight distribution.

The inventive compositions, uses and methods, and some preferred embodiments thereof are characterized by the following points:

1. Cosmetic composition for coloring keratinic fibers containing at least two separately packaged formulations (A) and (B), which are mixed immediately prior to application to give an application mixture, whereby the formulation (A) contains at least one dye from the group consisting of oxidation dye precursors and direct dyes, the formulation (B) is a flowable composition comprising water and at least one oxidizing agent, characterized in that the formulation (A) has been packaged in a water-soluble film consisting, based on its total weight, to an extent of at least about 60% by weight of a polymer mixture having a multimodal molecular weight distribution.

2. Cosmetic compositions according to point 1, characterized in that the water-soluble film consists, based on its total weight, to an extent of at least about 70% by weight, preferably to an extent of at least about 80% by weight, more preferably to an extent of at least about 90% by weight, and in particular to an extent of at least about 95% by weight of a polymer mixture having a multimodal molecular weight distribution.

3. Cosmetic compositions according to any of the preceding points, characterized in that the polymer mixture consists, based on its total weight, of a mixture comprising at least about 60% by weight, preferably at least about 80% by weight, more preferably at least about 90% by weight, quite preferably at least about 95% by weight a1) water-soluble vinyl alcohol/ninyl acetate copolymer a1) and a2) at least one water-soluble vinyl alcohol/vinyl acetate copolymer a2) different from the water-soluble vinyl alcohol/ninyl acetate copolymer a1).

4. Cosmetic compositions according to any of the preceding points, characterized in that the polymer mixture consists, based on its total weight, of a mixture comprising at least about 60% by weight, preferably at least about 80% by weight, more preferably at least about 90% by weight, quite preferably at least about 95% by weight a1) water-soluble vinyl alcohol/ninyl acetate copolymer a1) and a2) at least one optionally modified water-soluble polysaccharide, preferably at least one water-soluble polysaccharide from the group of methyl cellulose, carboxymethyl cellulose, ethyl cellulose, hydroxyethyl cellulose, hydroxypropyl cellulose, hydroxypropyl methylcellulose, dextrin, and hydroxypropyl starch, quite preferably at least one water-soluble polysaccharide from the group of hydroxypropyl starches.

5. Cosmetic compositions according to any of the preceding points, characterized in that the polymer mixture has a polydispersity index of greater than about 2.2, preferably greater than about 3.0, and in particular greater than about 4.6.

6. Cosmetic compositions according to any of the preceding points, characterized in that the vinyl alcohol/vinyl acetate copolymer a1) has a polydispersity index of between about 1.8 and about 2.3.

7. Cosmetic compositions according to any of the preceding points, characterized in that the vinyl alcohol/vinyl acetate copolymer a1) has a degree of hydrolysis between about 84% and about 90%, preferably between about 85% and about 89%, and in particular between about 86% and about 88%.

8. Cosmetic compositions according to any of the preceding points, characterized in that the vinyl alcohol/vinyl acetate copolymer a1) has a viscosity (20° C., 4% by weight solution in water, measured using a Brookfield LV Viscosimeter with UL adapter) of between about 12 cP and about 20 cP, preferably between about 14 cP and about 19 cP, and in particular between about 16 cP and about 18 cP.

9. Cosmetic compositions according to any of the preceding points, characterized in that the vinyl alcohol/vinyl acetate copolymer a2) has a viscosity (20° C., 4% by weight solution in water, measured using a Brookfield LV Viscosimeter with UL adapter) of between about 20 cP and about 30 cP, preferably between about 20 cP and about 28 cP, and in particular between about 20 cP and about 25 cP.

10. Cosmetic compositions according to any of the preceding points, characterized in that the water-soluble film, based on its total weight, has a water content of from about 3.0 to about 12% by weight, preferably from about 4.0 to about 10% by weight.

11. Cosmetic compositions according to any of the preceding points, characterized in that the water-soluble film has a thickness of from about 0.01 to about 0.1 mm, preferably from about 0.01 to about 0.08 mm, and in particular from about 0.02 to about 0.06 mm.

12. Cosmetic compositions according to any of the preceding points, characterized in that the weight ratio of formulation (A) to formulation (B) is about 2:1 to about 1:100, preferably about 2:1 to about 1:10, and in particular from about 2:1 to about 1:3.

13. Cosmetic compositions according to one of the preceding points, characterized in that formulation (A), based on its weight, contains from about 0.1 to about 10% by weight, preferably about 0.2 to about 8.0% by weight, and in particular from about 0.5 to about 6.0% by weight dyes from the group consisting of oxidation dye precursors and direct dyes, preferably oxidation dye precursors.

14. Cosmetic compositions according to any of the preceding points, characterized in that formulation (A) contains at least one oxidation dye precursor of the developer type, preferably at least one compound from the group consisting of p-toluenediamine, 2-(2-hydroxyethyl)-p-phenylenediamine, N,N-bis-(2-hydroxyethyl)-p-phenylenediamine, 2-methoxymethyl-p-phenylenediamine and/or their physiologically compatible salts.

15. Cosmetic compositions according to any of the preceding points, characterized in that formulation (A) contains at least one oxidation dye precursor of the developer type, preferably at least one compound from the group consisting of bis-(2-hydroxy-5-aminophenyl)methane, p-aminophenol, 4- and amino-3-methylphenol and/or their physiologically compatible salts.

16. Cosmetic compositions according to any of the preceding points, characterized in that formulation (A) contains at least one oxidation dye precursor of the developer type, preferably at least one compound from the group consisting of 4,5-diamino-1-(2-hydroxyethyl)pyrazole, 2,4,5,6-tetraaminopyrimidine, 4-hydroxy-2,5,6-triaminopyrimidine and/or their physiologically compatible salts.

17. Cosmetic compositions according to any of the preceding points, characterized in that formulation (A) contains at least one oxidation dye precursor of the coupler type, preferably at least one compound from the group consisting of 3-aminophenol, 5-amino-2-methylphenol, 3-amino-2-chloro-6-methylphenol, 2,4-dichloro-3-aminophenol and/or their physiologically compatible salts.

18. Cosmetic compositions according to any of the preceding points, characterized in that formulation (A) contains at least one oxidation dye precursor of the coupler type, preferably at least compound from the group consisting of 2-(2,4-diaminophenoxy)ethanol, 1,3-bis(2,4-di-aminophenoxy)propane, 1-methoxy-2-amino-4-(2-hydroxyethylamino)benzene, 2,6-bis(2'-hydroxyethylamino)-1-methylbenzene and/or their physiologically compatible salts.

19. Cosmetic compositions according to any of the preceding points, characterized in that formulation (A) contains at least one oxidation dye precursor of the coupler type, preferably at least one compound from the group consisting of resorcinol, 2-methylresorcinol, and 4-chlororesorcinol.

20. Cosmetic compositions according to any of the preceding points, characterized in that formulation (A) contains at least one oxidation dye precursor of the coupler type, preferably at least one compound from the group consisting of 2-amino-3-hydroxypyridine, 3-amino-2-methylamino-6-methoxypyridine, 2,6-dihydroxy-3,4-dimethylpyridine and/or their physiologically compatible salts.

21. Cosmetic compositions according to any of the preceding points, characterized in that formulation (A) contains at least one oxidation dye precursor of the coupler type, preferably at least one compound from the group consisting of 2-naphthol and 2,7-dihydroxynaphthalene.

22. Cosmetic compositions according to any of the preceding points, characterized in that formulation (B), based on its weight, contains about 50 to about 98% by weight, preferably about 60 to about 95% by weight, more preferably about 70 to about 88% by weight water, and, calculated as 100% H2O2, contains about 0.5 to about 20% by weight, preferably about 1 to about 15% by weight, particularly preferably about 2 to about 12% by weight hydrogen peroxide.

23. Cosmetic compositions according to any of the preceding points, characterized in that formulation (B), based on its weight, contains less than about 20% by weight, preferably less than about 10% by weight, and in particular less than about 5.0% by weight fatty substances.

24. Method for changing the color of keratinic fibers, in which at least two separately packaged formulations (A) and (B) are mixed immediately prior to application to give an application mixture, and in which the formulation (A), packaged in a water-soluble film, is dissolved and incorporated into the formulation (B), whereby
the formulation (A) contains at least one dye from the group of oxidation dye precursors and the direct dyes,
the formulation (B) is a flowable composition containing water and at least one oxidizing agent,
characterized in that the formulation (A) has been packaged in a water-soluble film consisting, based on its total weight, to an extent of at least about 60% by weight of a polymer mixture having a multimodal molecular weight distribution.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for lightening the color of keratinic fibers, comprising at least two separately packaged formulations (A) and (B), which are mixed immediately prior to application to give an application mixture, whereby
the formulation (A) comprises at least one dye chosen from the group of oxidation dye precursors, and direct dyes, or a combination thereof,
the formulation (B) is a flowable composition comprising water and at least one oxidizing agent,
wherein the formulation (A) has been packaged in a water-soluble film comprising, based on its total weight, at least about 60% by weight of a polymer mixture having a multimodal molecular weight distribution.

2. The cosmetic composition according to claim 1, wherein the polymer mixture comprises, based on its total weight, at least about 60% by weight
a1) water-soluble vinyl alcohol/vinyl acetate copolymer a1) and
a2) at least one water-soluble vinyl alcohol/vinyl acetate copolymer a2) different from the water-soluble vinyl alcohol/vinyl acetate copolymer a1).

3. The cosmetic composition according to claim 1, wherein the polymer mixture comprises, based on its total weight, at least about 60% by weight
a1) water-soluble vinyl alcohol/vinyl acetate copolymer a1) and a2) at least one optionally modified water-soluble polysaccharide.

4. The cosmetic composition according to claim 1, wherein the polymer mixture has a polydispersity index of greater than about 2.2.

5. The cosmetic composition according to claim 2, wherein the vinyl alcohol/vinyl acetate copolymer a1) has a degree of hydrolysis between about 84% and about 90%.

6. The cosmetic composition according to claim 1, wherein the water-soluble film has a thickness from about 0.01 to about 0.1 mm.

7. The cosmetic composition according to claim 1, wherein the weight ratio of formulation (A) to formulation (B) is from about 2:1 to about 1:100.

8. The cosmetic composition according to claim 1, wherein, based on its weight, formulation (A) comprises from about 0.1 to about 10% by weight dyes chosen from the group of oxidation dye precursors, direct dyes, or combinations thereof.

9. The cosmetic composition according to claim 1, wherein, based on its weight, formulation (B) comprises less than about 20% by weight fatty substances.

10. A method for changing the color of keratinic fibers, wherein the method comprises mixing at least two separately packaged formulations (A) and (B) immediately prior to application to give an application mixture, and in which formulation (A), packaged in a water-soluble film, is dissolved and incorporated into the formulation (B), whereby
formulation (A) comprises at least one dye chosen from the group of oxidation dye precursors, direct dyes, or combinations thereof,
formulation (B) is a flowable composition comprising water and at least one oxidizing agent,
wherein formulation (A) has been packaged in a water-soluble film comprising, based on its total weight, at least about 60% by weight of a polymer mixture having a multimodal molecular weight distribution.

11. The cosmetic composition according to claim 1, wherein the polymer mixture comprises, based on its total weight, at least about 95% by weight
a1) water-soluble vinyl alcohol/vinyl acetate copolymer a1) and
a2) at least one water-soluble vinyl alcohol/vinyl acetate copolymer a2) different from the water-soluble vinyl alcohol/vinyl acetate copolymer a1).

12. The cosmetic composition according to claim 1, wherein the polymer mixture comprises at least about 95% by weight
a1) water-soluble vinyl alcohol/vinyl acetate copolymer a1) and
a2) at least one optionally modified water-soluble polysaccharide chosen from the group of methyl cellulose, carboxymethyl cellulose, ethyl cellulose, hydroxyethyl cellulose, hydroxypropyl cellulose, hydroxypropyl methylcellulose, dextrin, and hydroxypropyl starch.

13. The cosmetic composition according to claim 1, wherein the polymer mixture has a polydispersity index of greater than about 4.6.

14. The cosmetic composition according to claim 2, wherein the vinyl alcohol/vinyl acetate copolymer a1) has a degree of hydrolysis between about 86% and about 88%.

15. The cosmetic composition according to claim 1, wherein the water-soluble film has a thickness from about 0.02 to about 0.06 mm.

16. The cosmetic composition according to claim 1, wherein the weight ratio of formulation (A) to formulation (B) is about 2:1 to about 1:3.

17. The cosmetic composition according to claim 1, wherein, based on its weight, formulation (A) comprises from about 0.5 to about 6.0% by weight dyes chosen from the group of oxidation dye precursors and direct dyes.

18. The cosmetic composition according to claim 1, wherein, based on its weight, formulation (B) comprises less than about 5.0% by weight fatty substances.

19. The cosmetic composition according to claim 1, wherein the weight ratio of formulation (A) to formulation (B) is about 2:1 to about 1:3; wherein formulation (A), based on its weight, comprises from about 0.5 to about 6.0% by weight dyes chosen from the group of oxidation dye precursors and direct dyes; and wherein, based on its weight, formulation (B) comprises less than about 5.0% by weight fatty substances.

20. A cosmetic composition for lightening the color of keratinic fibers, comprising at least two separately packaged formulations (A) and (B), which are mixed immediately prior to application to give an application mixture, whereby
the formulation (A) comprises, based on its weight, from about 0.1 to about 10% by weight of at least one dye chosen from the group of oxidation dye precursors, direct dyes, or a combination thereof,
the composition (B) is a flowable composition comprising water and at least one oxidizing agent, wherein, based on its weight, formulation (B) comprises less than about 20% by weight fatty substances;
wherein the weight ratio of formulation (A) to formulation (B) is about 2:1 to about 1:100;
wherein formulation (A) has been packaged in a water-soluble film comprising, based on its total weight, at least about 60% by weight of a polymer mixture having a multimodal molecular weight distribution, wherein the polymer mixture has a polydispersity index of greater than about 2.2, and wherein the water-soluble film has a thickness from about 0.01 to about 0.1 mm.

* * * * *